United States Patent [19]

Butterfield

[11] 4,392,852
[45] Jul. 12, 1983

[54] TAMPER-ALERTING HYPODERMIC SYRINGE

[75] Inventor: Ida M. Butterfield, Santa Maria, Calif.

[73] Assignee: Butterfield Group, Santa Maria, Calif.

[21] Appl. No.: 363,926

[22] Filed: Mar. 31, 1982

[51] Int. Cl.³ .............................................. A61M 5/00
[52] U.S. Cl. .................................................... 604/111
[58] Field of Search ................... 604/111, 93, 38, 183, 604/218, 219, 220, 221, 222, 228

[56] References Cited

U.S. PATENT DOCUMENTS

| | | | |
|---|---|---|---|
| 2,658,837 | 11/1953 | Blackman | 128/218 C |
| 2,869,541 | 1/1959 | Helmer | 128/218 C |
| 2,888,015 | 5/1959 | Hunt | 128/218 C |
| 3,126,004 | 3/1964 | Sarnoff | 128/218 P |
| 3,934,586 | 1/1976 | Easton et al. | 128/218 C X |
| 3,951,146 | 4/1976 | Arias | 128/218 P X |

Primary Examiner—John D. Yasko
Attorney, Agent, or Firm—Daniel C. McKown

[57] ABSTRACT

The inside surface of the glass tubular member of the hypodermic syringe cartridge is made rough along a strip which extends substantially the length of the cartridge. A piece of a solid but easily abradable material is retained on the circumference of the rubber drive piston, and the resiliency of the rubber drive piston squeezes the abradable material against the rough strip on the inside wall of the glass tubular member. As the drive piston is advanced to express fluid from the syringe, some of the abradable material becomes lodged in the rough surface where it remains even after the drive piston has been retracted to its original position. In another embodiment the marking substance is a fluid, paste, or liquid which is stored in a reservoir inside the drive piston and which is squeezed out of the drive piston by the compressive forces that act on the drive piston as it is being advanced.

4 Claims, 4 Drawing Figures

TAMPER-ALERTING HYPODERMIC SYRINGE

BACKGROUND OF THE INVENTION

1. Field of the Invention

The present invention is in the field of medical apparatus and more specifically relates to an improvement in a hypodermic syringe to permit the user of the syringe to determine readily whether the syringe has been tampered with.

2. The Prior Art

In a hypodermic syringe cartridge of the type known in the prior art, a rubber drive piston is mounted within a tubular glass member that serves as a container for an injectable fluid. The drive piston includes a front face that is in contact with the fluid in the cartridge. Typically, a small screw is embedded in the rubber drive piston and extends through the rear face of the drive piston. The purpose of this screw is to permit an actuator rod to be connected to the drive piston. The injectable fluid is expelled from the syringe when the user pushes on the actuator rod thereby causing the drive piston to advance against the fluid.

There have been instances where persons have removed narcotics from such a syringe without authorization, and have then replaced the pilfered fluid with a substitute fluid. In order to accomplish this, it is necessary for the drive piston to be advanced against the fluid so as to express some of the fluid into another container and thereafter, the tip of the hypodermic needle is inserted into a substitute fluid which is then aspirated into the hypodermic syringe cartridge by retracting the drive piston in the direction opposite to the direction in which it was originally advanced. After this sequence has been carried out on a cartridge of the type used in the prior art, it is practically impossible to detect that the cartridge has been tampered with. The present invention is an improvement to a hypodermic syringe cartridge which will alert a later user of the cartridge to the fact that the cartridged has previously been tampered with.

SUMMARY OF THE INVENTION

In accordance with the present invention, the inside surface of the glass tubular member of the hypodermic syringe cartridge is made rough along a strip which extends substantially the length of the cartridge. A piece of a solid but easily abradable material is retained on the circumference of the rubber drive piston, and the resiliency of the rubber drive piston squeezes the abradable material against the rough strip on the inside wall of the glass tubular member. As the drive piston is advanced to express fluid from the syringe, some of the abradable material becomes lodged in the rough surface where it remains even after the drive piston has been retracted to its original position. In a preferred embodiment of the present invention, the abradable material is visually conspicuous so that a later user of the syringe can readily observe a visually conspicuous strip of the readily abradable material that has been deposited on the rough strip.

In another embodiment the marking substance is a fluid, paste, or liquid which is stored in a reservoir inside the drive piston and which is squeezed out of the drive piston by the compressive forces that act on the drive piston as it is being advanced.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
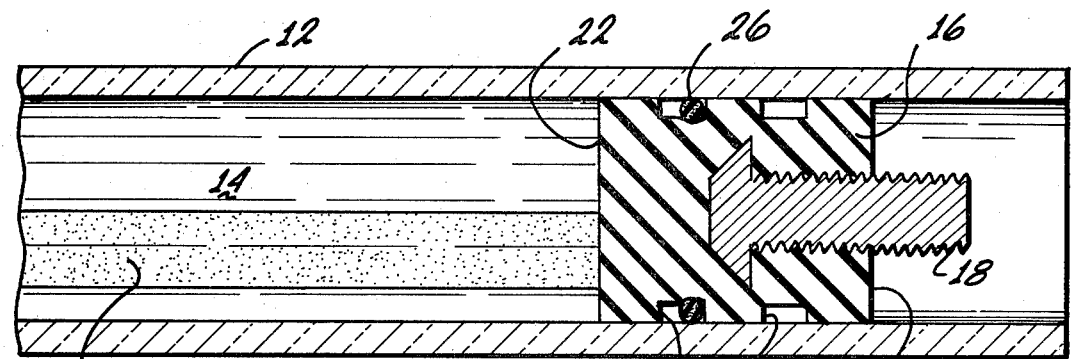
FIG. 1 is a fractional cross-sectional view of a hypodermic syringe cartridge in which a preferred embodiment of the improvement of the present invention has been installed, shown in the unused condition in which the cartridge is normally supplied.
Figure 2:
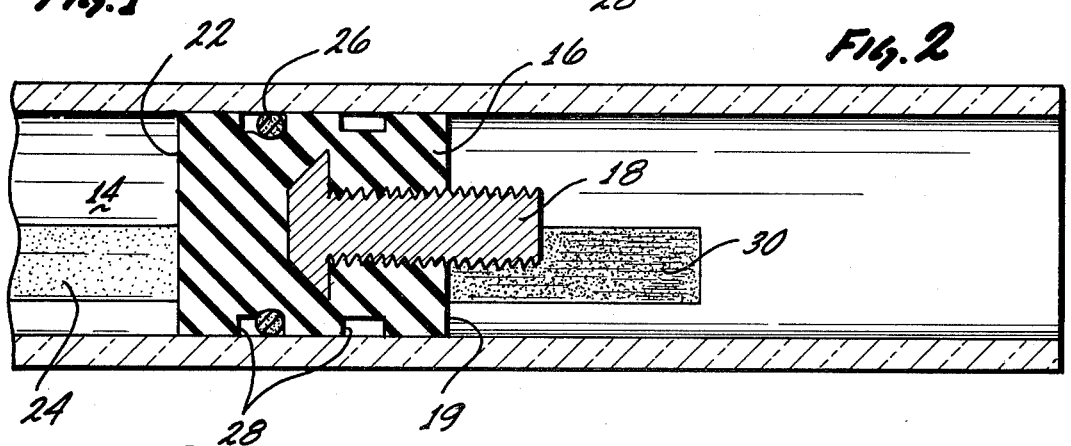
FIG. 2 is a fractional cross-sectional view of the cartridge of FIG. 1 after the drive piston has been advanced in use.
Figure 3:
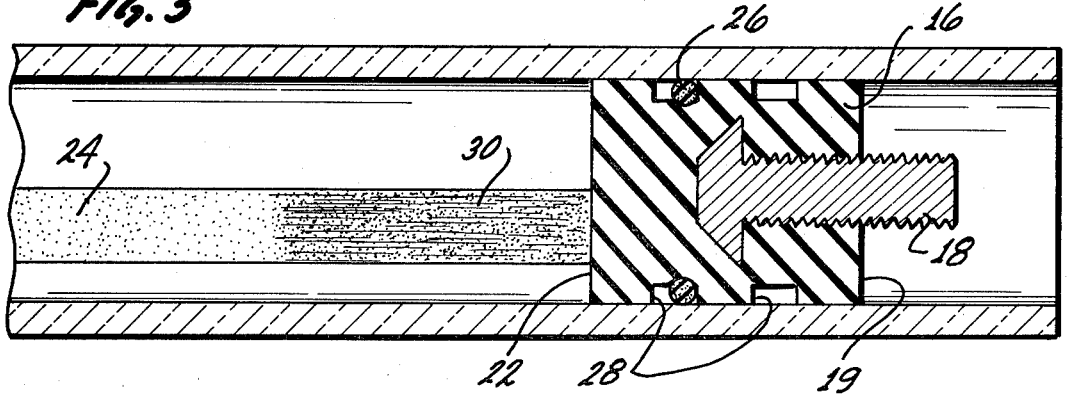
FIG. 3 is a fractional cross-sectional view showing the cartridge of FIGS. 1 and 2 after the drive piston has been retracted to its original psition; and, FIG. 4 is a fractional cross-sectional view of a hypodermic syringe cartridge in which an alternative embodiment of the improvement of the present invention has been installed, shown in the unused condition in which the cartridge is normally supplied.

FIGS. 1, 2 and 3 all show the same hypodermic syringe cartridge but at successive stages in its use. For clarity, the actuator rod has been omitted from the drawings. The rod has a threaded socket in its end. The user inserts the actuator rod through the open right-hand end of the tubular member 12 and rotates the actuator rod about its axis to screw it onto the screw 18 which is embedded in the drive piston 16.

The improvement of the present invention includes two modifications of the cartridge used in the prior art. First, a portion 24 of the inside wall 20 of the tubular member 12 is made rough, for example by etching. In a preferred embodiment of the present invention, the rough portion 24 has the shape of a strip which extends longitudinally throughout substantially the entire length of the cartridge. Second, the improvement of the present invention includes one or more pieces 26 of a readily abradable material which is lodged between the drive piston 16 and the tubular member 12. In the preferred embodiment, the pieces 26 of abradable material are retained in one of the grooves 28 that run circumferentially around the drive piston 16.

In a preferred embodiment, the abradable material is a wax that has been colored brightly by means of a harmless dye. In other embodiments, graphite and colored pencil leads have been found to produce the desired effect.

In the manufacturing process, the tubular member 12 is first etched or sandblasted to produce the rough portion 24, and later a quantity of the desired fluid 14 is introduced into the tubular member 12. Thereafter, the drive piston 16 and the pieces 26 of abradable material are introduced from the right hand end as viewed in the figures. In the preferred embodiment, the pieces 26 of abradable material are separate from the drive piston 16 and are slightly larger radially than the grooves 28 in which the pieces 26 are retained. This causes some deformation of the rubber of the drive piston 16 when the drive piston is inserted in the tubular member 12. The elastic restoring forces of the rubber drive piston 16 continually urge the pieces 26 of abradable material radially outward against the inside wall 20 of the tubular member 12.

In an alternative embodiment, the pieces 26 of abradable material are molded into the drive piston 16 so as to be inseparable from it. In that embodiment, before assembly, the pieces 26 extend radially to a greater distance than the radius of the inside wall 20, so that in the alternative embodiment, after assembly, the pieces 26 are urged against the inside wall 20 by the elastic restoring forces of the rubber drive piston 16. FIG. 1 shows the preferred embodiment of the invention in the unused condition.

As the drive piston 16 is pushed to the left to express some of the fluid from the syringe cartridge, the pieces 26 of abradable material rub against the rough portion 24 of the inside wall 20 of the tubular member 21. Some of the abradable material becomes embedded in the microscopic irregularities of the rough portion 24 and thereby impart to the rough portion 24 a visually conspicuous appearance, as indicated by the portion 30 of FIG. 2. FIG. 2 shows the cartridge after the drive piston 16 has been advanced some distance.

After some of the fluid 14 has been expressed from the syringe cartridge, the user may retract the drive piston 16 to its original position as shown in FIG. 3. This may be done for the purpose of aspirating a substitute fluid into the cartridge to conceal the theft of the original contents. However, as shown in FIG. 3, the reverse movement of the drive piston 16 does not remove the abradable material that was deposited on the rough portion 24, but instead the abradable material remains embedded in the rough portion, and the section 30 remains as a visually conspicuous indication of the extent of the motion of the drive piston, as shown in FIG. 3. Anyone later picking up the hypodermic syringe would be alerted to the fact that it has been tampered with.

Figure 4:
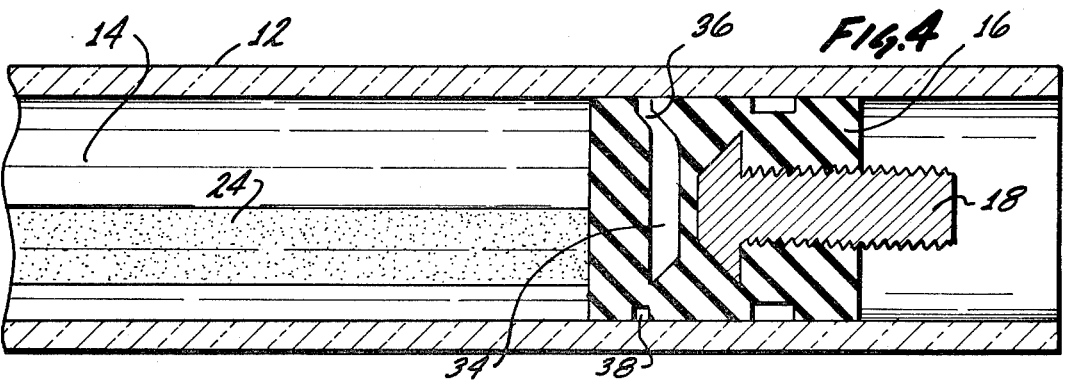

FIG. 4 shows an alternative embodiment of the improvement of the present invention. In this embodiment the marking substance is a fluid, paste or liquid 32, preferably visually conspicuous. The paste is held in a cavity 34 inside the drive piston. The cavity 34 communicates with a circumferential groove 38 or other port on the cylindrical outside surface of the drive piston 16 through one or more passages of which the passage 36 is typical.

When a force is applied to the screw 18 to advance the drive piston 16 leftward as viewed in FIG. 4, that force is opposed by the fluid 14. The cavity 34 is squeezed by these forces, urging the paste 32 to flow out of the cavity 34 through the passage 36 and into the circumferential groove 38. The paste in the groove 38 comes in contact with the rough strip 24 and clings tenaciously to it, thereby leaving a relatively permanent deposit on the strip.

Thus, there has been described a preferred embodiment and an alternative embodiment of a tamper-alerting hypodermic syringe in which a forward motion of the drive piston leaves a relatively permanent mark on the inside surface of the tubular member. The foregoing detailed description illustrates a preferred embodiment of the invention and it is to be understood that additional embodiments will be obvious to those skilled in the art. The embodiments described herein together with those additional embodiments are considered to be within the scope of the invention.

What is claimed is:

1. An improvement for use in a hypodermic syringe of the type having a drive piston slidably mounted in a tubular member, said improvement comprising:
   a piece of easily abradable material mounted on the drive piston for motion with the drive piston and urged radially outward by the drive piston against the inside surface of the tubular member; and,
   a rough area on the inside surface of the tubular member in the form of a strip extending lengthwise of the tubular member, whereby as the drive piston is advanced within the tubular member said piece of easily abradable material rubs on said rough area causing particles of the easily abradable material to become securely lodged on said rough area where their presence provides a relatively permanent indication of the extent to which the drive piston has been advanced.

2. The improvement of claim 1 wherein said easily abradable material is a visually conspicuous material.

3. An improvement for use in a hypodermic syringe of the type having a drive piston slidably mounted in a tubular member and advanced within the tubular member by a pushing force applied to a screw that is embedded in the drive piston, said improvement comprising:
   a cavity located ahead of the screw in the drive piston;
   a port on the cylindrical outside surface of the drive piston;
   a passage connecting said cavity with said port;
   a marking fluid stored in said cavity; and,
   a rough area on the inside surface of the tubular member extending lengthwise of the tubular member, whereby when a force is applied to the screw to advance the drive piston in the tubular member, some of said marking fluid is squeezed out of the cavity, through the passage, and out through the port where said marking fluid leaves a relatively permanent deposit on said rough area.

4. The improvement of claim 3 wherein said marking fluid is visually conspicuous.

* * * * *